United States Patent [19]
Sandborn et al.

[11] Patent Number: 5,846,983
[45] Date of Patent: Dec. 8, 1998

[54] COLONIC DELIVERY OF NICOTINE TO TREAT INFLAMMATORY BOWEL DISEASE

[75] Inventors: William J. Sandborn, Rochester, Minn.; John Rhodes, Cardiff, Great Britain

[73] Assignee: Mayo Foundation for Medical Education and Research, Rochester, Minn.

[21] Appl. No.: 605,319

[22] Filed: Feb. 9, 1996

[51] Int. Cl.⁶ .................................................. A01N 43/40
[52] U.S. Cl. ...................... 514/343; 546/279.4; 523/100; 524/102
[58] Field of Search .................. 514/343; 546/279.4; 523/100; 524/102

[56] References Cited

U.S. PATENT DOCUMENTS

| | | | |
|---|---|---|---|
| 4,855,142 | 8/1989 | Fankhauser et al. | 424/434 |
| 5,604,231 | 2/1997 | Smith et al. | 514/256 |

FOREIGN PATENT DOCUMENTS

| | | |
|---|---|---|
| 377520 | 7/1990 | European Pat. Off. |
| 92/01457 | 2/1992 | WIPO |
| 92/14452 | 9/1992 | WIPO |
| WO9427576 | 12/1994 | WIPO |

OTHER PUBLICATIONS

Thomas, G. A. O., et al, Eur. J. Gastroenterol, 8, 769–776 (1996).
Lichtiger S., et al, N. Engl. J. Med. 330, No. 26, 1841–1845 (Jun. 30, 1994).
Sandborn, W. J., et al, Gastroenterology, 108, 1429–1435 (1994).
Thomas, G. A. O., et al, N. Engl. J. Med., 332, No. 15, 988–992 (Apr. 19, 1995).
Lichtiger, S., et al, Gastroenterology, vol. 104, No. 4, Part 2, p. A732 AGA Abstracts (Apr. 1993).
Zins, B. J., et al, Gastroenterology, vol. 110, No. 4, p. A1054 (Apr. 1996).
Cecil Textbook of Medicine, 19th edition, edited by Wyngaarden, J.B. et al, W.B. Saunders Co., pp. 699–708, Oct. 1992.
Handbook of Pharmaceutical Excipients, 2nd edition, 363.
Danish Budesinode Study Group, Scand J. Gastroent., 1991, 26, pp. 1225–1230.
Winter, T.A. et al, Scand. J. Gastroent., 1993, 28(8), pp. 701–704, abstract only.
"Noncompartmental Analysis Based on Statistical Momemt Theory", *Pharmacokinetics*, 2nd ed., M. Gibaldi (ed), Marcel Dekker Inc., New York, pp. 409–417, (1982).
"Rectal Topical Corticosteroid Preparations", *Drug and Therapeutics Bulletin*, 29, Publ. Consumer' Association, London, pp. 66–68, (1991).
N. L. Benowitz, et al., "Stable Isotope Studies of Nicotine Kinetics and Bioavailability", *Clin. Pharmacol. Ther.*, 49, 270–277, (1991).
M. H. Brock, et al., "Use of In Vitro and In Vivo Data in the Design, Development, and Quality Control of Sustained–Release Decongestant Dosage Forms", *Pharmacotherapy*, 14, 430–437, (1994).
P. Dominiak, et al., "Effects of nicotine and its major metabolites on blood pressure in anesthetized rate", *Klin. Wochenschr.*, 63, 90–92 (1985),.
M. J. Durrani, et al., "Studies on Drug Release Kinetics from Carbopol 934P Tablets", *Pharmaceutical Res. (Suppl.)*, 8, S–135, (1991).
S. Edsbacker, et al., "Pharmacokinetics and Gastrointestinal Transit of Budesonide Controlled Ileal Release (CIR) Capsules", *Gastroenterology (Supp)*, 104, A695, (Apr. 1993).
D. F. Glenn, et al., "Synthesis and Mass Spectrometry of Some Structurally Related Nicotinoids", *J. Org. Chem.*, 43, 2860–70, (1978).
G. R. Greenberg, et al., "Oral Budesonide for Active Crohn's Disease", *NEJM*, 331, 836–41, (1994).
D. A. Hutton, et al., "Mucolysis of the Colonic Mucus Barrier By Faecal Proteinases: Inhibition by Interacting Polyacrylate", *Clin. Sci.* 78, 265–271, (1990).
L. G. Miller, et al., "Reversible Alterations in Immunoregulatory T Cells in Smoking", *Chest*, 82, No. 5, 526–529, (1982).
R. D. Pullan, et al., "Comparison of Bismuth Citrate and 5–aminosalicylic Acid Enemas in Distal Ulcerative Colitis: A Controlled Trial", *Gut*, 34, 676–679, (1993).
R. D. Pullan, et al., "Transdermal Nicotine for Active Ulcerative Colitis", *NEJM*, 330, No. 12, 811–815, (Mar. 24, 1994).
C. J. Roberts, et al., "Non–smoking: A Feature of Ulcerative Colitis", *Br. Med. J.*, 285, 440, (1982).
W. J. Sandborn, et al., "The Pharmokinetics and Colonic Tissue Concentrations of Cyclosporine After IV, Oral, and Enema Administration", *J. Clin. Pharmacol.*, 31, 76–80, (1991).
K. W. Schroeder, et al., "Coated Oral 5–Aminosalicylic Acid Therapy for Mildly to Moderately Active Ulcerative Colitis", *NEJM*, 317, 1625–29, (1987).
E. D. Srivastava, et al., "Transdermal Nicotine in Active Ulcerative Colitis", *Eur. J. Gastro. & Hepat.*, 3, 815–818, (1991).
L. R. Sutherland, "Topical Treatment of Ulcerative Colitis", *Medical Clinics of North America*, 74, 119–131, (1990).
G. A. O. Thomas, "Nicotine Therapy for Ulcerative Colitis", Dissertation for the degree of Doctor of Medicine, London University, (Jul. 1995).

*Primary Examiner*—John Kight
*Assistant Examiner*—Garth Dahlen

[57] ABSTRACT

A method is provided to treat inflammatory bowel disease by locally administering to the colon an effective amount of nicotine or a pharmaceutically acceptable salt thereof, preferably via formulations adapted for delayed oral release or rectal administration. Further provided is a novel formulation for the oral administration of nicotine comprising a polyacrylic polymer complexed with nicotine.

15 Claims, 6 Drawing Sheets

COLONIC DELIVERY OF NICOTINE TO TREAT INFLAMMATORY BOWEL DISEASE

The invention was made with the support of Grant Nos. FD-T-000-886 and M01-RR00585 awarded by the U.S. department of Public Health Services. The U.S. Government has certain rights in the invention.

BACKGROUND OF THE INVENTION

Inflammatory bowel disorders or diseases (IBD) encompass a spectrum of overlapping clinical diseases that appear to lack a common etiology. IBD, however, are characterized by chronic inflammation at various sites in the gastrointestinal (GI) tract. Illustrative IBD are regional enteritis (or Crohn's disease), idiopathic ulcerative colitis, idiopathic proctocolitis, pouchitis and infectious colitis. Symptoms of IBD may include persistent diarrhea, abdominal pain, fever, weight loss, joint pain, skin lesions and general fatigue. The inflammatory conditions of ulcerative colitis are confined to the colon, unlike Crohn's disease which can involve any portion of the intestinal tract.

Studies have suggested that an important epidemiolgic link exists between ulcerative colitis (UC) and a patient's smoking history. Several investigators have reported that the prevalence of UC in non-smokers is higher than in current smokers. In addition, studies have suggested that ex-smokers are at even greater risk than life-time smokers for developing UC. It further appears that lifetime non-smokers exposed in childhood to passive tobacco smoke have a greater risk of developing ulcerative colitis than non-exposed lifetime non-smokers.

The observations that active colitis improves with smoking has led to investigational use of nicotine as a therapeutic agent for colitis (Roberts et al., *Br. Med. J.* 285:440 (1982); Srivastava et al., *Eur. J Gastro. & Hepat.* 3:815–6 (1991)). However, long term nicotine administration by way of polacrilex gum or transdermal patch has limitations due to systemic side effects as well as those inherent to the specific administration vehicles. For example, nicotine administered as chewing gum results in variable absorption and a wide range of plasma nicotine levels. Long term use of the transdermal patch is limited by a relatively high rate of dermatologic side effects. General side effects of nicotine administration can include nausea, vomiting, headaches, insomnia, somnolence, diaphoresis, pre-syncope and tremor.

Thus, a need exists for a safe and effective method of treating IBD.

SUMMARY OF THE INVENTION

The present invention provides a therapeutic method of treating inflammatory bowel disease (IBD) comprising locally administering to the rectum, colon and/or terminal ileum of a patient in need of such treatment, an amount of nicotine effective to reduce the symptoms of IBD. In one embodiment of the present method, the nicotine is administered orally, by means of a unit dosage form that selectively releases nicotine in the terminal ileum and/or colon of the patient. On another embodiment of the method, the nicotine can be effectively administered to the colon by rectal administration of an enema formulation or rectal foam comprising nicotine. Nicotine can also be delivered to the ileum or colon of an IBD patient by administration of an enterically coated unit dosage form. The present invention also provides a novel composition particularly suitable for the colonic administration of nicotine comprising crosslinked polyacrylic acid polymers complexed with nicotine.

DETAILED DESCRIPTION OF THE INVENTION

Figure 1:
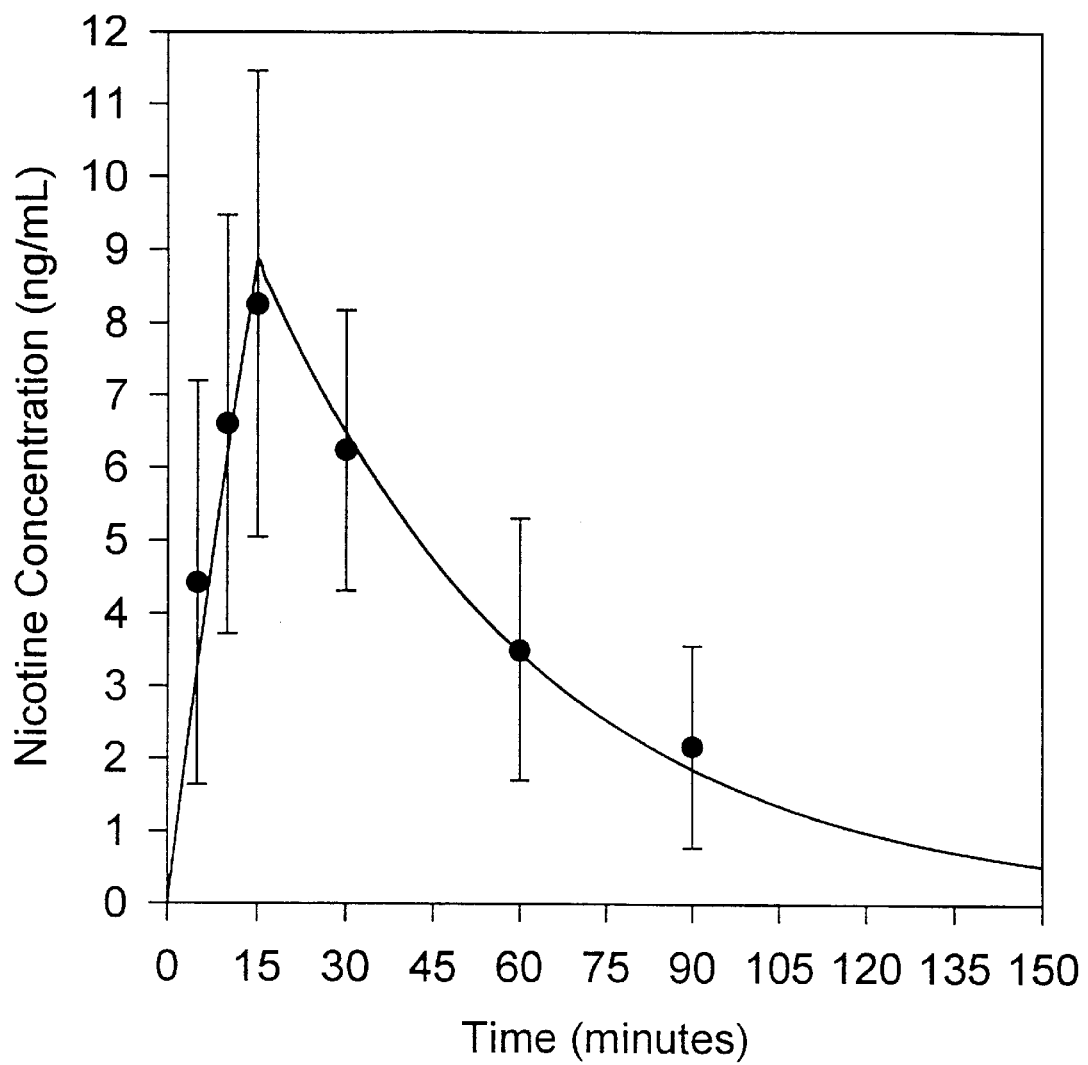
FIG. 1 shows mean plasma concentration-time curve during intravenous administration of 15 mcg nicotine/Kg body weight over 15–30 minutes.
Figure 2:
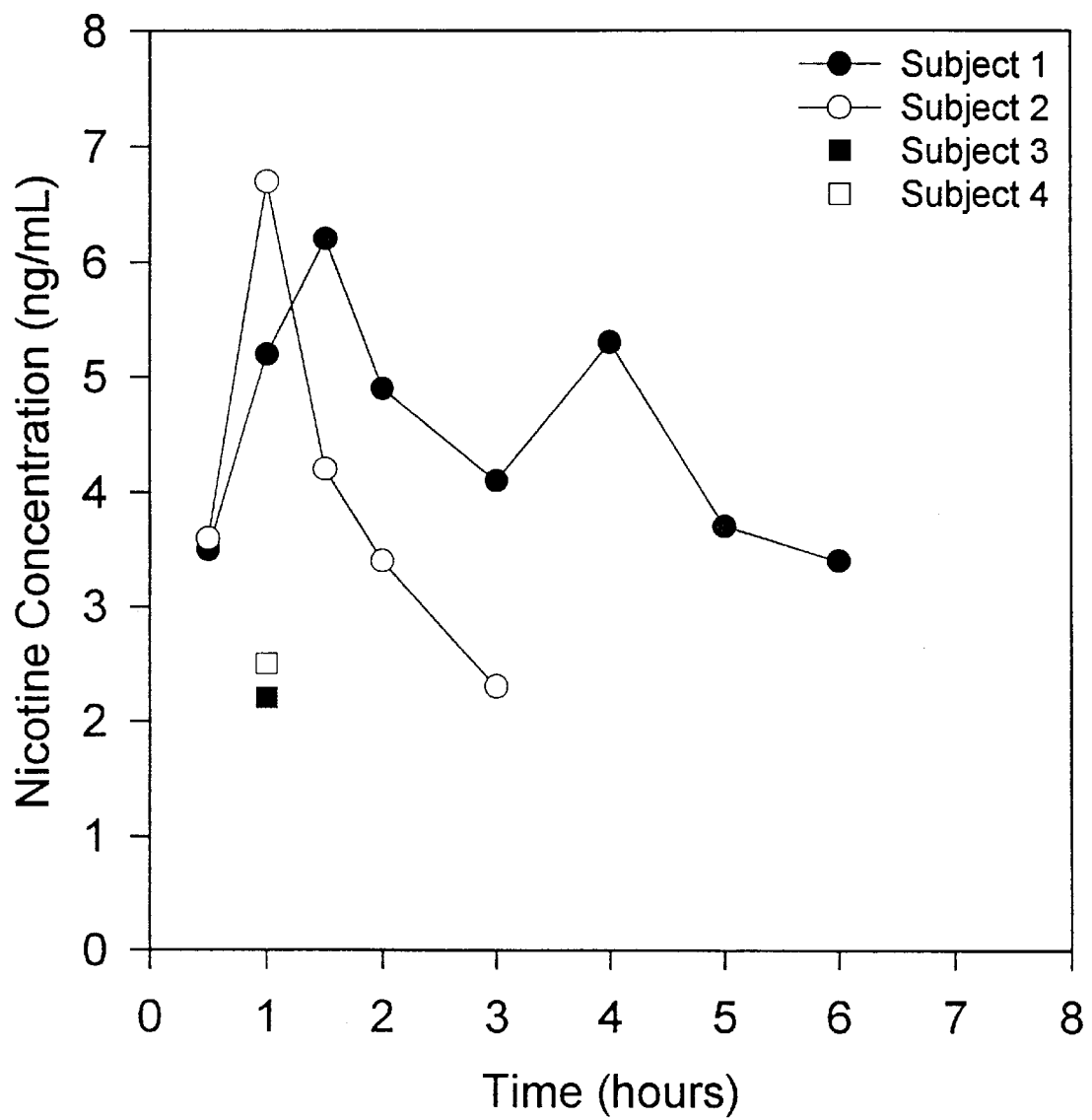
FIG. 2 shows plasma concentration-time curve after oral administration of 45 mcg nicotine/Kg body weight for each subject with detectable levels (2 subjects had no detectable levels).
Figure 3:
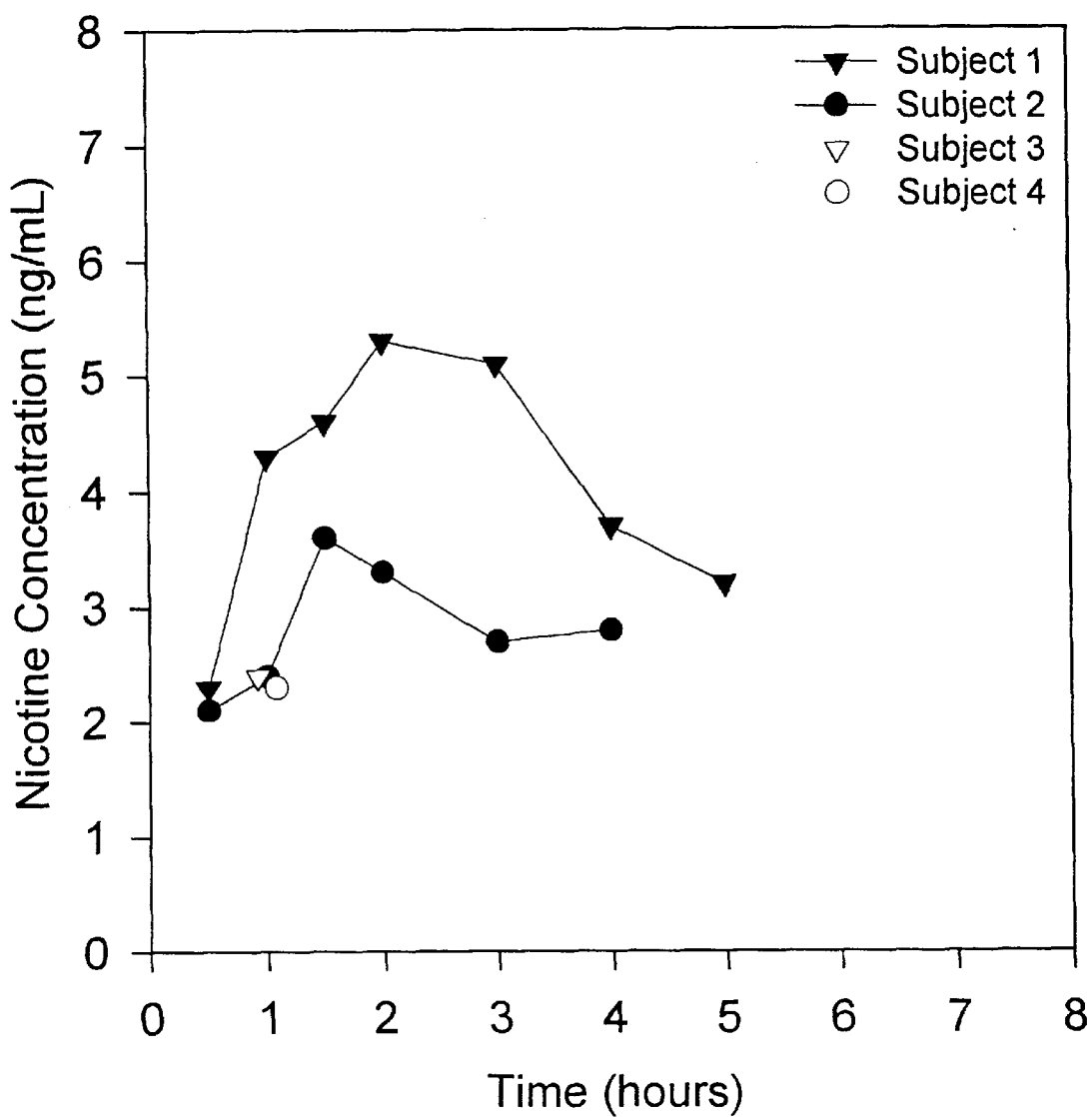
FIG. 3 shows plasma concentration-time curve after administration via hydrophilic acidic enema vehicle of 45 mcg nicotine/Kg body weight for each subject with detectable levels (2 subjects had no detectable levels).
Figure 4:
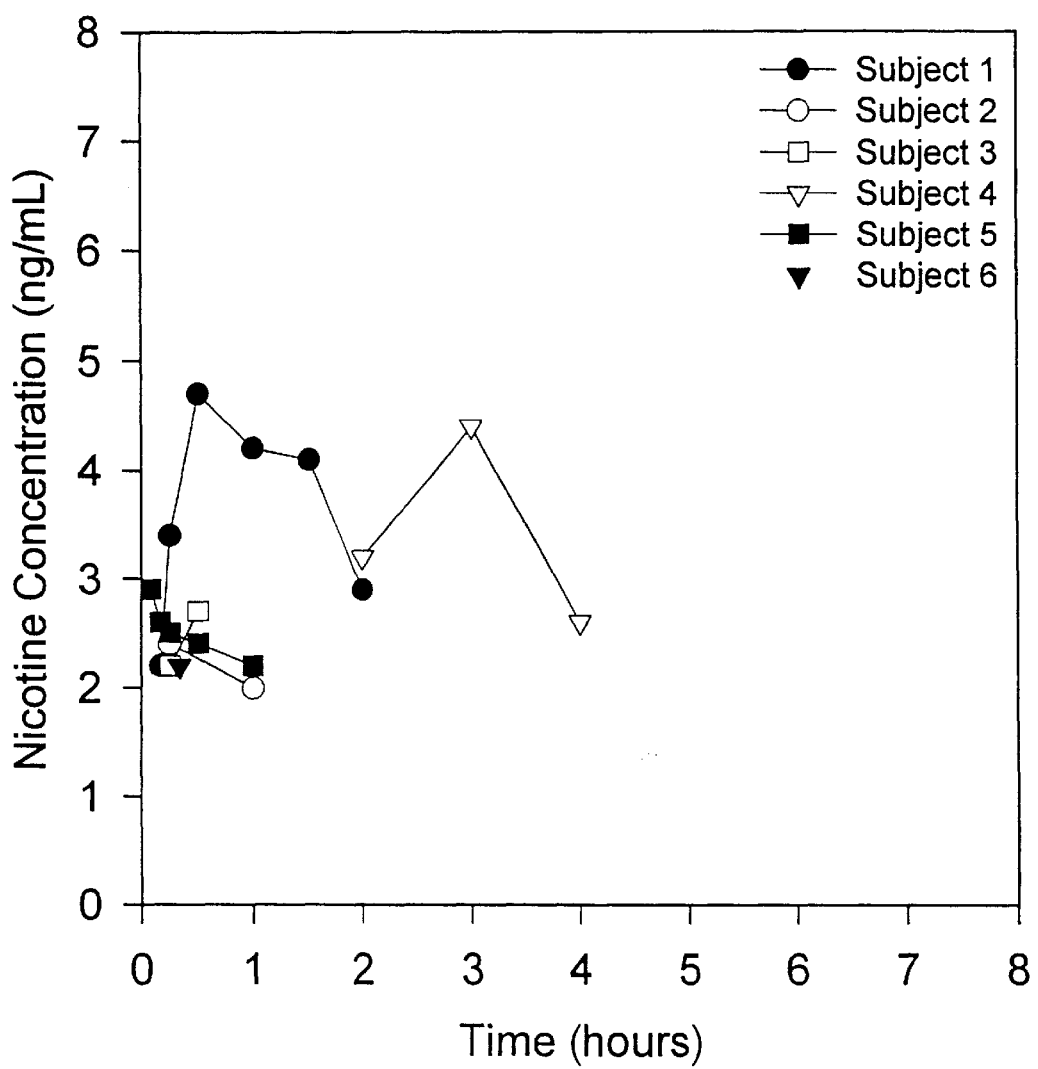
FIG. 4 shows plasma concentration-time curve after administration via hydrophilic basic enema vehicle of 45 mcg nicotine/Kg body weight for each subject with detectable levels (1 subject had no detectable levels).
Figure 5:
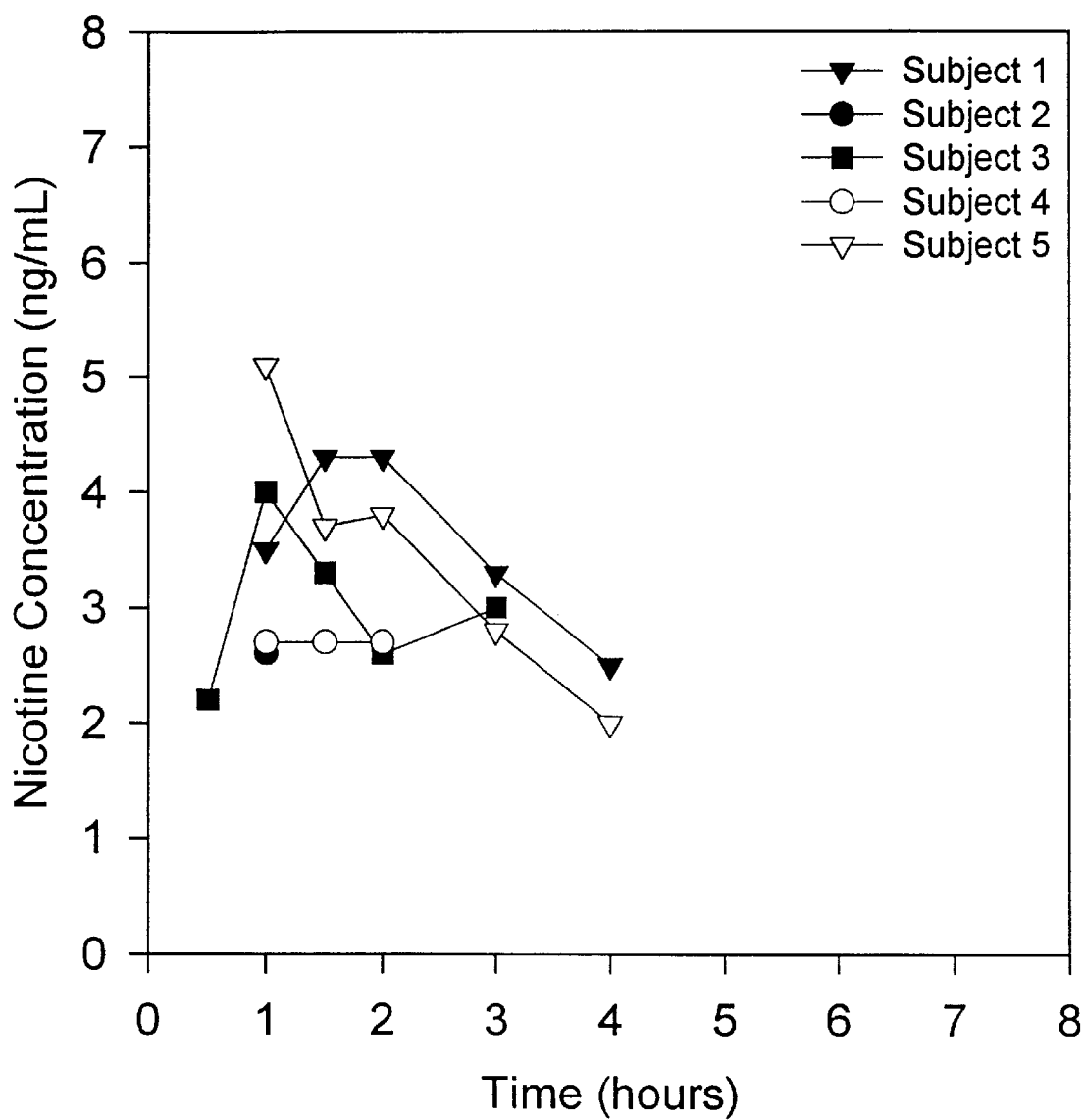
FIG. 5 shows plasma concentration-time curve after administration via hydrophobic acidic enema vehicle of 45 mcg nicotine/Kg body weight for each subject with detectable levels (1 subject had no detectable levels).
Figure 6:
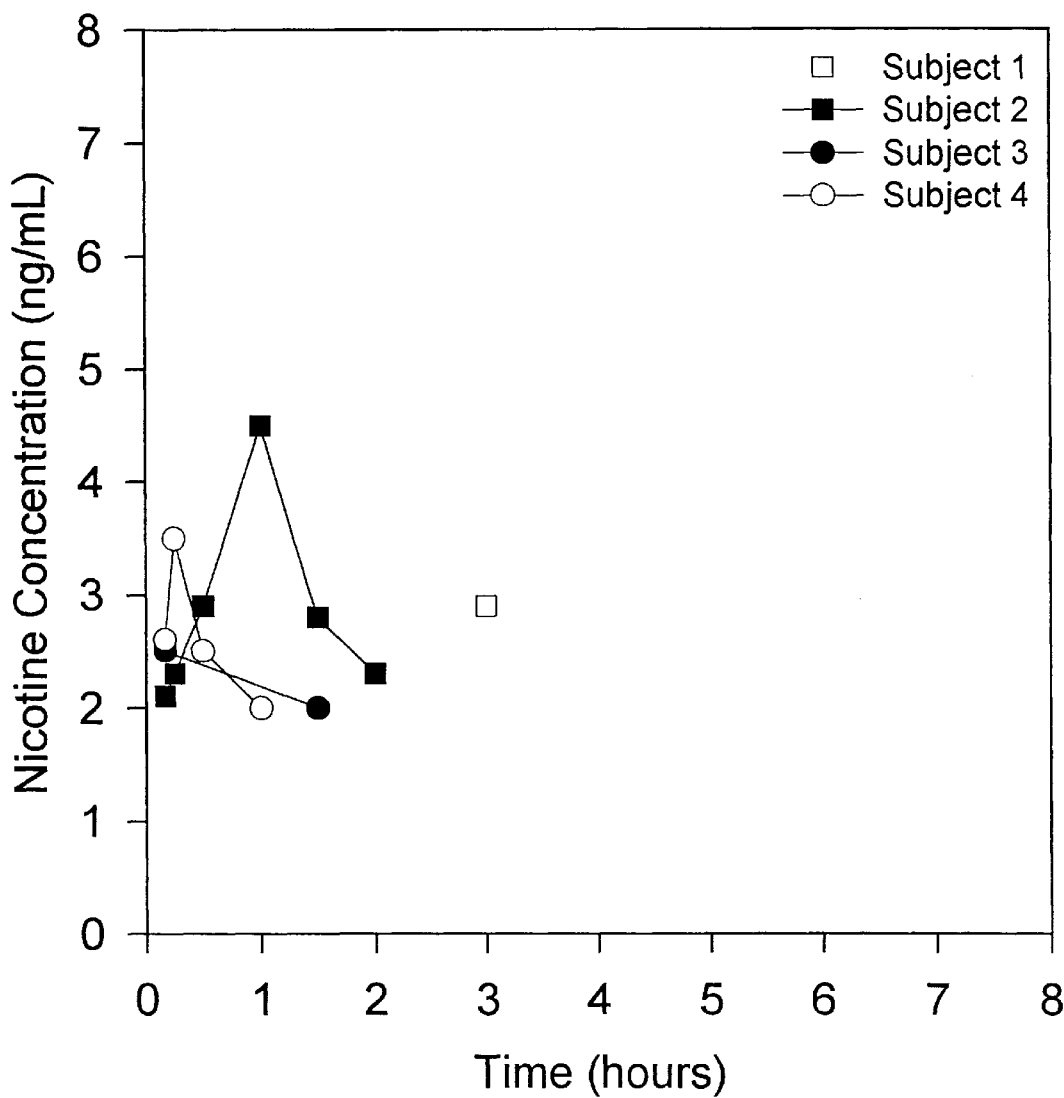
FIG. 6 shows plasma concentration-time curve after administration via hydrophobic basic enema vehicle of 45 mcg nicotine/Kg body weight for each subject with detectable levels (2 subjects had no detectable levels).

Nicotine is an organic compound which is derived from tobacco leaves, and comprises a pyridine (hydrophilic) and a pyrrolidine (hydrophobic) ring which enable it to form solutions in a wide variety of solvents including water, alcohol, ether, chloroform, kerosine and oils. The nicotine base (liquid at room temperature) is quite volatile and is readily absorbed through mucous membranes and intact skin. Nicotine salts (crystalline at room temperature), on the contrary, are very stable and not absorbed through the skin. For example, nicotine bitartrate salt consists of a single nicotine molecule in conjunction with two tartrate molecules and a single water molecule. This compound has been previously used in oral and IV pharmacokinetics trials (Miller et al., *Chest* 5:527 (1982); Benowitz et al., *Clin. PharmacoL Ther.* 49:270 (1991)).

Any pharmacologically acceptable derivative or metabolite of nicotine which exhibits pharmacotherapeutic properties similar to nicotine may also be used in practicing the invention. Such derivatives and metabolites are known in the art (Glenn et al. *J Org Chem.,* 43:2860–2870 (1978); Dominiak et al., *Klin Wochenschr,* 63:90–92 (1985)) and include nicotine oxide and cotinine.

Any pharmaceutically acceptable acid or metal salt of nicotine may be used in practicing the present invention. A particular characteristic property of nicotine is its ability to form salts with almost any acid and double salts with many metals and acids. The acids that may be used to prepare the pharmaceutically acceptable acid salts of nicotine are those that form non-toxic acid salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate, ethanesulfonate, benzenesulfonate, p-toluene sulfonate, camphorate and pamoate salts.

Although it is unknown how nicotine might act to treat ulcerative colitis, a number of possibilities exist. First, nicotine has been shown to suppress both humoral and cellular immunity and these immunosuppressive properties might have some therapeutic impact in ulcerative colitis.

Second, leukotriene mediated inflammation appears to be important in the pathogenesis of colitis. Nicotine appears to reduce mucosal production of eicosanoids including prostaglandin E, 6-keto-PGF1a, leukotriene B4, and leukotriene C4/D4/E4.

Third, colonic mucus production has been shown to be qualitatively and quantitatively abnormal in patients with colitis. However, nicotine appears to increase mucus synthesis to levels observed in healthy subjects. In addition, rabbits receiving high doses of nicotine have greater mucus thickness as compared to controls.

Fourth, nicotine increases circulating ACTH and plasma cortisol. This increase in endogenous corticosteroids may have some beneficial effect on colitis. Interestingly, this effect is attenuated by exogenous steroid administration.

Finally, it has been reported that patients with ulcerative colitis have a significantly higher rectal blood flow than controls and that nicotine can reduce rectal blood flow to the normal range.

Colonic administration of drugs has been used to reduce the toxicity associated with oral or IV corticosteroids and oral 5-aminosalicylic acid in patients with IBD (Edsbacker et al., *Gastroenterology* 104:A695 (1993); Greenberg et al., *NEJM* 331:836–41 (1994); Schroeder et al., *NEJM* 317:1625–29 (1987)). This decreased toxicity is believed to be due to reduced systemic bioavailability. Colonic administration of nicotine can reduce systemic bioavailability consequently decreasing side effects and improving patient tolerance of nicotine treatment.

Several types of colonic drug delivery systems are currently available, including enemas (Sutherland et al., *Med. Clin. North Amer.,* 74:119 (1990)); rectal foams (*Drug Ther. Bull.,* 29:66 (1991)); and delayed oral release formulations in the form of enteric-coated capsules which disintegrate at pH 7 in the terminal ileum (Schroeder et al., *NEJM*, 317:1625 (1987)).

According to one preferred embodiment of the present method, nicotine is administered to the colon in the form of an enema formulation, which is rectally administered to the lower colon. Useful enema formulations comprise an effective amount of nicotine dissolved or dispersed in a suitable flowable carrier vehicle, such as water, alcohol or an aqueous-alcoholic fluid. The carrier vehicle is preferably thickened with natural or synthetic thickeners such as gums, acrylates or modified celluloses. The formulation can also comprise an effective amount of a lubricant such as a natural or synthetic fat or oil, i.e., a tris-fatty acid glycerate or lecithin. Nontoxic nonionic surfactants can also be included as wetting agents and dispersants. Unit dosages of enema formulations can be administered from prefilled bags or syringes. The carrier vehicle may also comprise an effective amount of a foaming agent such as n-butane, propane or i-butane. Such formulations can be delivered from a pre-loaded syringe pressurized container, so that the vehicle is delivered to the colon as a foam, which inhibits its escape from the target site.

In a further preferred embodiment, nicotine is administered via oral ingestion. The effective amount of nicotine can be locally administered to the colon of the patient by oral ingestion of a unit dosage form such as a pill, tablet or capsule, comprising an effective amount of nicotine which is enterically coated so as to be released from the unit dosage form in the lower intestinal tract, e.g., in the ileum and in the colon of the patient. Enteric coatings remain intact in the stomach, but will dissolve and release the contents of the dosage form once it reaches the region where the pH is optimal for dissolution of the coating used. The purpose of an enteric coating is to substantially delay the release of the nicotine until it reaches its target site of action in the ileum or colon. Since nicotine locally administered to the colonic tissue in this fashion is only about 20% absorbed in the bloodstream (based on rectal administration), the systemic side-effects of nicotine can be avoided or minimized.

Aqueous film-coating technology is employed for the enteric coating of pharmaceutical dosage forms. Delayed-released oral nicotine dosage forms have the potential advantage of delivering nearly all the nicotine to the ileum or colon in an easily administered form which can theoretically avoid the increased systemic rectal absorption seen with enemas. In addition, enterically coated nicotine will not have the dermatologic side effects directly related to patch delivery.

Thus, a useful enteric coating is one that remains intact in the low pH environment of the stomach, but readily dissolved when the optimum dissolution pH of the particular coating is reached. This can vary between pH 3 to 7.5 depending upon the chemical composition of the enteric coating. The thickness of the coating will depend upon the solubility characteristics of the coating material and the site to be treated.

The most extensively used polymer for enteric coating is cellulose acetate phthalate (CAP). However, CAP has an optimum dissolution pH greater than 6, thus early drug release may occur. Another useful polymer is polyvinyl acetate phthalate (PVAP) which is less permeable to moisture and gastric fluid, more stable to hydrolysis and able to dissolve at a lower pH, which could also result in early release of nicotine in the doudenum.

Another available polymer is hydroxypropyl methylcellulose phthalate. This has similar stability to PVAP and dissociates in the same pH range. Further examples of currently used polymers are those based on methacrylic acid, e.g., methacrylic acid ester copolymers with acidic ionizable groups, such as Eudragit L, S or LS and mixtures thereof, the choice dependent upon the site of required dissolution of the coating. Dosage forms coated with Eudragit, which dissolve in the ileum at about pH 6.8, and in the terminal ileum and caecum at about pH 7.2, have been developed and have been used in the delivery of 5-aminosalicylic acid.

A dosage form of nicotine adapted for either rectal or oral delivery may also be complexed with a suspending or thickening agent to prolong release of the dosage form of nicotine. Such agents include acrylic acid polymers, preferably carbomers (carboxypolymethylene) which are synthetic high molecular weight acrylic acid polymers crosslinked with polyfunctional moieties such as polyallylsucrose. Generally, carbomers comprise 50 to 70% carboxylic acid groups.

On ingestion of a suitably formulated solid oral dosage form, carbomers hydrate and swell to form a gel, which retards drug release and absorption. Carbomers are mucoadhesive and adhere to colonic mucus thereby potentially maximizing the nicotine/carbomer effect on the colonic mucosa but are not absorbed systemically. As carbomers adhere strongly to mucus membranes in gel form, they serve as excellent topical or local delivery vehicles for bioactive compounds. They have been shown to promote gel formation with mucin monomers from both gastric and colonic mucus (Pullan et al., *Gut,* 34:676–9 (1993)). In the colon they also inhibit fecal protease activity, which is responsible for mucolysis and solubilization of the adherent layer of mucus gel. Carbomers' inhibition of mucolysis strengthens the colonic mucus barrier, which is deficient in ulcerative colitis and may play a role in its pathogenesis (Hutton et al., *Clin. Sci.,* 78:265–71 (1990)).

Carbomers are available as fine white powders which disperse in water to form acidic colloidal suspensions (a 1% dispersion has approx. pH 3) of low viscosity. Neutralization of these suspensions using a base, for example sodium, potassium or ammonium hydroxides, low molecular weight amines and alkanolamines, results in the formation of clear translucent gels. Nicotine salts such as nicotine chloride form stable water-soluble complexes with carbomers at about pH 3.5 and are stabilized at an optimal pH of about 5.6.

In one embodiment of the invention, the carbomer is Carbopol. Such polymers are commercially available from B.F. Goodrich under the designation Carbopol 420, 430, 475, 488, 493, 910, 934, 934P and the like. Carbopols are versatile controlled-release polymers, as described by Brock (*Pharmacotherapy,* 14:430–7 (1994)) and Durrani (*Pharmaceutical Res.* (*Supp.*) 8:S-135 (1991)), and belong to a family of carbomers which are synthetic, high molecular weight, non-linear polymers of acrylic acid, crosslinked with polyalkenyl polyether. In a particularly preferred embodiment the carbomer is Carbopol® 974P NF.

To prepare nicotine/carbomer complexes, the carbomer is suspended in an appropriate solvent, such as water, alcohol or glycerin. Preferably, the carbomer is mixed with water, preferably de-ionized water. Mixtures may range, for example, from 0.002 to 0.2 grams of carbomer per mL of solvent, preferably from 0.02 to 0.1 grams of carbomer per mL of solvent. The mixture is stirred thoroughly at room temperature until a colloidal suspension forms. The dispersion may be stirred using a suitable mixer with a blade-type impeller, and the powder slowly sieved into the vortex created by the stirrer using a 500 micron brass sieve. This technique allows ample wetting of the powder and prevents the powder from forming a cluster of particles which then become difficult to wet and disperse.

The nicotine or nicotine salt may be diluted with any pharmaceutically acceptable organic solvent. In a preferred embodiment, the solvent is an alkanol such as ethanol. Mixtures may range, for example, from 0.01 to 10 grams of nicotine per mL of solvent, preferably from 0.5 to 5 grams of nicotine per mL solvent. This solution is then added drop wise to the carbomer suspension and mixed continuously until a gel of uniform consistency has formed. Preferably, the nicotine/complex is made by combining 1 gram of nicotine or nicotine salt with from 0.1 to 100 grams of carbomer, more preferably with 1 to 50 grams of carbomer. A gradual thickening of the suspension may occur as neutralization of the carbomer takes place. The complex will also become white. This physical change in viscosity is consistent with neutralization of the acid by the base.

The gel is then dried. According to one embodiment, the gel is vacuum dried. By way of example, the gel is spread on a glass plate and dried under vacuum at 50° C. for about 24 hours. Alternatively, the gel may be freeze-dried. Such methods are well known in the art.

Nicotine/carbomer complexes can then be formed into solid dosage forms and a pharmaceutically acceptable coating may be applied, as described above for non-complexed nicotine. For example, the complex may be enterically coated thereby delaying the release of the nicotine/carbomer complex until it reaches the ileum and colon; and thus maximizing its local effect on the colon. The nicotine/carbomer complex will likely not be absorbed and this theoretically will prolong and enhance the effect of nicotine on the colonic mucosa. The capsule may be coated with a Eudragit film and the contents themselves coated either as a powder or as microgranules or microspheres.

In addition to being orally administered, the nicotine/carbomer complexes may be administered rectally as liquid enemas. Liquid enemas are prepared essentially as described above by adding an effective amount of a nicotine/carbomer complex to a suitable flowable liquid carrier. The carrier vehicle is preferably thickened with thickeners and can also comprise an effective amount of a lubricant. Unit dosages of enema formulations can be administered from prefilled bags or syringes. Carbomers alone may have some therapeutic role in ulcerative colitis, when given as an enema.

It will be appreciated that the amount of nicotine, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, where the nicotine is administered rectally, a suitable dose will be in the range of from about 0.001 to about 1.5 mg/Kg, preferably in the range of 0.01 to 0.20 mg/Kg, most preferably in the range of 0.04 to 0.10 mg/Kg, calculated as nicotine in the free base form. Preferably, nicotine is rectally administered once or twice daily.

In general, where the nicotine is administered orally, a suitable dose will be in the range of from about 0.001 to about 1.5 mg/Kg, preferably in the range of 0.01 to 0.20 mg/Kg, most preferably in the range of 0.04 to 0.10 mg/Kg, calculated as nicotine in the free base form. Preferably, nicotine is orally administered 1 to 4 times daily, more preferably 3–4 times daily, although more frequent dosing is contemplated where hourly dosing is desired.

The compound is conveniently administered orally in unit dosage form; for example, containing 0.10 to 20 mg, conveniently 0.5 to 10 mg, most conveniently, 3 to 6 mg of active ingredient per unit dosage form.

Studies described herein compare the bioavailability and pharmacokinetics parameters of nicotine after administration by each of 6 different routes: IV; oral; hydrophilic enema (acidic and basic); and hydrophobic enema (acidic and basic). Thirty (30) healthy volunteers were enrolled in this prospective randomized study. All subjects underwent 2 investigations (IV and non-IV) at least one week apart. Subjects were divided equally among the 5 non-IV groups: hydrophilic rectal enema (acidic or basic); hydrophobic rectal enema (acidic or basic); and oral. Plasma nicotine concentrations were measured before and during the 8 hour period following administration.

The mean bioavailability for the oral route was 19 (10%); the mean bioavailability for rectal enemas were: hydrophilic acidic 16 (7%); hydrophilic basic 14 (6%); hydrophobic acidic 25 (7%); and hydrophobic basic 15 (4%). There was no statistical difference in bioavailability between the 5 delivery routes and all 5 were significantly less than the bioavailability for IV nicotine 100 (0% ($p<0.01$). Side effects directly correlated with plasma nicotine concentrations. Thus, oral and colonic administration of nicotine had low or negligible bioavailability and was well tolerated.

The invention will be further described by reference to the following detailed examples.

EXAMPLES

Example I

This study compared the bioavailability and pharmacokinetics parameters of nicotine after administration by each of 6 different routes: IV; oral; hydrophilic enema (acidic and basic); and hydrophobic enema (acidic and basic).

Intravenous nicotine was prepared using a nicotine base, supplied as the tartrate salt (Fisher Scientific/Eastman Kodak Company, Rochester, N.Y.) Solutions for injection were made up by combining 1.5 mg nicotine base (4.44 mg tartrate salt) in 100 ml of 0.9% sterile normal saline to form a 15 mcg/mL solution. The intravenous solution was filtered through a 0.22 micron filter into a sterile container and under sterile conditions. The solution was then cultured for organisms, assayed for endotoxin, and chemically analyzed prior to infusion to assure stable nicotine concentration. These samples were then be stored in sealed vials until the time of administration.

The oral preparation was formed by dissolving 45 micrograms nicotine base/kg body weight (133.3 micrograms tartrate salt/kg body weight) in 30 ml purified water. This dosage (approximately 3 mg nicotine base for a 70 kg subject) has been well-tolerated in a previous study in which oral nicotine was administered (Benowitz et al., *Clin. Pharmacol. Ther.* 49:270–7 (1991)).

The hydrophilic enema vehicle was prepared by combining 500 mg of medium viscosity carboxymethylcellulose (Spectrum Chemical Manufacturing Corporation, Gardina, Calif.), 5 g sorbitol (Spectrum Chemical), and 60 mL of water. The sorbitol was added to make the vehicle isoosmolar and the carboxymethylcellulose was used as a suspending agent. The vehicle, described previously (Sandborn et al., *J Clin. Pharmacol.* 31:76–80 (1991)), was dispensed into 120 ml enema bottles. The active agent, 133.3 micrograms nicotine tartrate salt/kg body weight (equivalent to 45 micrograms nicotine base/kg body weight) was added to the enema vehicle.

The hydrophobic enema vehicle was prepared by adding 3 g of Witepsol H-15 (an oleaginous base—Huls American Inc., New Jersey) to the hydrophilic enema vehicle. Enema vehicles were made acidic by adding 5.06 g of sodium citrate dihydrate (Spectrum Chemical) and 0.56 g of citric acid monohydrate (Spectrum Chemical) to create a solution with a pH of 5.5. Enema vehicles were made basic by adding 5.23 g of sodium phosphate (Spectrum Chemical) and 0.05 g of sodium phosphate monobasic (Spectrum Chemical) to create a pH 8.5 solution. The enema vehicles were confirmed to be stable over a 48 hour time period (100% recovery) with a minimal decrease in nicotine concentration when allowed to stand at room temperature over a 3 week period (97% recovery at 1 week, 94% recovery at 2 weeks, 91% recovery at 3 weeks).

Thirty paid human volunteers were admitted to the pharmacokinetic study after giving informed consent to a protocol approved by the institutional review board at the Mayo Clinic, Rochester, Minn. The subjects ranged in age from 21–56 and their body weights ranged from 45 to 153 Kg. All subjects were non-smokers and were healthy based on their histories, and physical examination. Subjects agreed to practice birth control during the study period. Complete blood count, chemistry group, urinalysis and pregnancy test (women only) were obtained. Subjects were excluded if they had cardiovascular disease, peripheral vascular disease, hypertension, were nursing mothers, had laboratory evidence of pregnancy, or had hepatic or renal dysfunction.

Based on the results of a pilot study of two additional subjects, it was determined that colonic absorption of nicotine is dependent upon patient position, with higher plasma levels detected when subjects were allowed into a sitting position immediately after administration, rather than remaining in the left lateral decubitus position. The first subject studied underwent 3 investigations (IV, 15 mcg/Kg hydrophilic basic enema, 45 mcg/Kg hydrophilic basic enema). During the 15 mcg/Kg enema visit the subject was inadvertently allowed into a sitting position after administration and was found to have an AUC of 17 (ng)(hr)/mL (IV visit AUC 18 (ng)(hr)/mL) with a bioavailability of 94%. On the 45 mcg/Kg visit the subject remained in the left lateral decubitus position the entire time the enema was retained and had an AUC of 0 (ng)(hr)/mL with a bioavailability of 0%. Similarly, one subject withdrew from the study after the enema visit (first visit) in which an upright position was taken shortly after administration and side effects occurred. The AUC for this subjects visit was 18 (ng)(hr)/mL. During the remainder of the study, subject position was more closely monitored and plasma nicotine concentrations remained low or undetectable with enema administration.

Each subject underwent 2 investigations (IV and non-IV) of 8 hours duration at least 1 week apart. During the IV visit, subjects were given a 15–30 minute infusion of the IV nicotine solution (15 mcg/Kg dose). During the non-IV visit subjects were given a 45 mcg/Kg dose of nicotine base via one of five randomly selected delivery routes which were prepared within 48 hours of administration: oral; hydrophilic enema (acidic or basic); hydrophobic enema (acidic or basic). The subjects were instructed to remain in the left lateral decubitus position while the enema was retained and to retain the enema for at least one hour. On each study day, venous blood samples were drawn from an IV catheter into standard chemistry vacutainer tubes. Samples were obtained before nicotine administration and at the following time points (time=0 was defined as the point at which the nicotine infusion was started or the non-IV dose was administered): 5, 10, 15, 30, 60, 90 minutes, and 2, 3, 4, 5, 6, and 8 hours. Whole blood samples were centrifuged and plasma samples were then stored at -20 degrees Celsius until analysis. Plasma concentrations of nicotine were determined by gas chromatography/mass spectrometry as described by Baskin et al. (*Clin. Chem.,* 31:76–80 (1991)).

For this study, the maximum plasma nicotine concentration (Cmax) and the time to reach Cmax (Tmax) were defined as the highest measured plasma concentrations and the time of the sample, respectively. The following pharmacokinetics parameters were calculated using standard equations (Gibaldi (ed.) *Pharmcokinetics* 2nd ed, Marcel Dekker Inc., New York 409–17 (1982)): area under the plasma nicotine concentration versus time curve (AUC), bioavailability (F), blood elimination half-life (T1/2), volume of distribution (Vdss), and blood nicotine clearance (CLb).

The computed bioavailability for each subject was used in an analysis of covariance to compare the five groups. Within subject (IV versus non-IV) variation was evaluated for each group of 6 subjects using a paired-T test. In addition, data was reviewed for gender variation.

Mean plasma nicotine concentrations after IV is shown in FIG. 1. Plasma nicotine concentrations after oral, hydrophilic acidic enema, hydrophilic basic enema, hydrophobic acidic enema, and hydrophobic basic enema are shown in FIGS. 2 through 6, respectively. Nicotine was first detected in the plasma at 30 minutes with oral, hydrophilic acidic enema, and hydrophobic acidic enema administration, 10 minutes with hydrophobic basic enema administration, and 5 minutes with hydrophilic basic enema administration (when detectable levels were present).

The mean values for the pharmacokinetics parameters and statistical probability by analysis of covariance for nicotine administered by each of the various routes are shown in Table 1. No statistical differences were found in Cmax, AUC, and bioavailability when comparisons were made between enema and oral administration; however, Tmax for the hydrophilic basic enemas was significantly earlier than for the other 4 delivery systems. Finally, the mean bioavailability for the various routes of administration are as follows: oral 19%; hydrophilic acidic enema 16%; hydrophilic basic enema 14%; hydrophobic acidic enema 25%; hydrophobic basic enema 15%.

TABLE 1

|  | Subject (n) | AUC[+] (ng)(h)/mL | F % | $T_{max}$ hr | $C_{max}$ ng/mL |
|---|---|---|---|---|---|
| Oral | 6 | 9 ± 5 | 19 ± 10 | 1.1 ± 0.1 | 3 ± 1 |
| Hdrphbc Acid | 6 | 10 ± 3 | 25 ± 7 | 1.3 ± 0.2 | 3 ± 1 |
| Hdrphbc Base | 6 | 4 ± 1 | 15 ± 4 | 1.1 ± 0.5 | 2 ± 1 |
| Hrdrphlc Acid | 6 | 8 ± 4 | 16 + 7 | 1.4 ± 0.2 | 2 ± 1 |
| Hrdrphlc Base | 6 | 4 ± 2 | 14 ± 6 | 0.3 ± 0.1 | 2 ± 1 |
| P* |  | 0.834 | 0.830 | 0.023 | 0.885 |

*Analysis of corvariance adjusting for baseline.
[+]Analyzed on the natural log scale.
IV nicotine studies (n = 32) (mean ± SD): AUC = 12 ± 5 (ng)(hr)/mL; Cmax = 9 ± 3 ng/mL;
$T_{max}$ = 0.3 ± 0.1 h.

Intraindividual side effects occurred during each study, as determined by a questionnaire filled out every 30 minutes, closely correlated with plasma nicotine concentrations. However, the threshold above which symptoms appeared varied from individual to individual with the nicotine concentration at which side effects first appeared ranging from 2.4 ng/mL to 9.9 ng/mL (although some subjects had nicotine concentrations of >11 ng/mL without symptoms). When side effects occurred, they consisted of nausea, lightheadedness, and diaphoresis with variable frequency.

The pharmacokinetics parameters T1/2, Vdss, and CLb calculated for IV dosing in the current study are somewhat different from those previously reported by in the literature (see, e.g., Benowitz et al., Clin. Pharmacol. Ther. 49:270–7 (1991)). A shorter T1/2 (53 (27 min.) vs. 203 (61 min.)), smaller Vdss (1.8 (0.5 L/Kg) vs 3.0 (0.7 L/Kg)), and faster CLb (106 (46 L/hr) vs. 66 (8 L/hr)) was observed in the current study. The observed differences are most likely due to the different population of subjects studied (non-smokers in the current study vs. heavy smokers in the Benowitz study), as well as the different dose of nicotine administered (0.5 mcg/Kg in the current study vs. 2 mcg/Kg in the Benowitz study). Additionally, a lower mean bioavailability was observed for the oral dose in the current study 19 (10%) as compared to that observed by Benowitz et al. (44 (9%)).

The mean bioavailability for the enema preparations was low or negligible, although there was no statistically significant difference observed when compared to oral administration. Interestingly, neither pH nor the hydrophilicity or hydrophobicity of the enema vehicle impacted significantly on absorption (although the hydrophilic basic enema had a significantly earlier Cmax). Furthermore, in the previous studies in which the nicotine patch was successfully used in active UC (Pullan et al., NEJM 330:811–15 (1994)), the mean plasma nicotine levels were over 12 ng/mL which is 6 fold greater than the Cmax for the enema vehicles. This suggests that large doses of nicotine could be directly administered to the colonic mucosa in UC patients and potentially yield equivalent efficacy with decreased toxicity as compared to the nicotine patch.

During the course of the study, it was observed that the systemic bioavailability of the enema vehicles appeared to be highly dependent upon the position in which the subject remained while retaining the enema. Subjects that were allowed to sit upright shortly after enema delivery were observed to have a higher bioavailability than when remaining in the left lateral decubitus position. This presumably was due to rectal pooling of the enema with absorption directly into the systemic circulation rather than the portal circulation, thereby eliminating first pass metabolism by the liver. By virtue of the positional dependence of this preparation, formulation of a colonic delivery system which could avoid direct absorption by the hemorrhoidal circulation could be beneficial.

In conclusion, rectal administration of nicotine had low bioavailability and was well tolerated. Therefore, nicotine may be administered to the colon as a therapeutic agent for IBD without the limitations inherent to other modes of administration.

Example II

The goal of this study is to evaluate pharmacokinetics parameters, dose ranges, and safety of a single dose of nicotine administered to healthy human volunteers by the following routes: a) IV (0.5 microgram/kg/min for 30 min); b) Eudragit® (Eudragit) coated oral nicotine (3 mg nicotine); c) Eudragit coated oral nicotine (6 mg nicotine); and d) Eudragit coated oral nicotine complexed with Carbopol® 974P NF (6 mg nicotine).

Colonic administration of Eudragit coated oral nicotine (which dissolves in the terminal ileum) could potentially decrease side effects of nicotine. Nicotine complexed with Carbopol® 974P NF, a new nicotine/Carbopol molecule, may serve as a new treatment for ulcerative colitis with potentially negligible side effects as minimal absorption is expected.

Intravenous nicotine was prepared as described in Example I.

Delayed-release Eudragit coated oral nicotine capsules were prepared by Tillotts Pharma AG, Ziefen, Switzerland and consisted of either 3 mg or 6 mg of nicotine (9.206 mg or 18.412 mg nicotine tartrate base salt, respectively (taking into account 7.1% water content of the tartrate salt)). The nicotine salt was suspended in an excipient (a saturated polyglycolized glyceride; Gelucire 44/14, Gattefosse France)(190 mg or 380 mg, respectively) and filled into hard gelatine capsules (size 1). The capsules were then coated with Eudragit L30D. Eudragit L30D is a polymer which dissolves at about pH 6.8 in the ileum. The size of the capsule and the thickness of the Eudragit coating are similar to those used to deliver Asacol® (Eudragit coated mesalamine) to the terminal ileum (Schroeder et al., NEJM, 317:1625–9 (1987)).

Delayed-release Eudragit coated oral nicotine/Carbopol capsules were prepared by Tillotts Pharma. The nicotine/ carbomer powder (1:50—nicotine: carbomer) was coated with Eudragit S. The coated powder was filled into hard gelatine capsules (size 1) and the capsules were coated with Eudragit S. The capsules contain 150 mg nicotine/carbomer complex, equivalent to 3 mg nicotine base.

The levo (-) form of nicotine base was used to prepare the nicotine/Carbopol capsules. Nicotine was obtained from Sigma Chemicals at a 98–100% purity and a density of 1.02 g/mL. It was protected from light and stored in a cool place.

Carbopol 974P NF (1 g, 13.2 mmol carboxylic acid) was mixed with 50 mL of de-ionized water, stirred thoroughly and allowed to stand for 30 minutes at room temperature.

Meanwhile, nicotine (1 g, 17 drops from a Pasteur pipette) was diluted in 1 mL absolute ethanol. This solution was then added dropwise to the carbomer suspension and mixed continuously for approximately 10 minutes until a gel of uniform consistency had formed. Visual observation, during this process, noted a gradual thickening of the suspension occurring as neutralization of the carbopol took place. It was also accompanied by a white appearance of the product. This physical change in viscosity was consistent with neutralization of the acid by the base.

The gel was then spread on a large glass plate and dried under vacuum at 50° C. for 24 hrs. The resulting white crystalline material was crushed using a pestle and mortar. The yield was 1.45 g (72.5%) after prolonged drying of the ground crystals.

An alternative method of drying to elevated temperature is freeze-drying. On repeating the above manufacture and freeze-drying the product, the yield increased to 1.65 g (82.5%). This yield increase was probably due to reduced volatilization of the nicotine component.

Larger batches were prepared as follows: 50 g of carbopol powder was weighed and dispersed in 2500 mL of de-ionized water. The dispersion was rapidly stirred using a suitable mixer with a blade-type impeller.

The powder was slowly sieved into the vortex created by the stirrer using a 500 micron brass sieve. Meanwhile, 1 g of nicotine was accurately measured and diluted with 1 mL of absolute ethanol. After the carbomer powder had been allowed to form a colloidal suspension for 30 min., the stirring speed was greatly reduced to get rid of the majority of air bubbles that had formed throughout the preparation. The alcoholic nicotine solution was then added drop wise into the vortex and stirring continued for 60 min. At the end of this time the batch was freeze-dried. This product could then be used to prepare batches of Eudragit coated powder.

Thin layer chromatography (TLC) was run and stained with Dragondorff reagent, a non-specific stain of NH and $NH_2$ groups. The nicotine ran with the carbomer, distinct from nicotine alone, showing that the nicotine was at least "bound" to the carbomer.

The nicotine/carbomer complex may also be administered using an enema formulation. A carbomer colloidal suspension was prepared as described above (400 mg of Carbopol 974P in de-ionized water). To this suspension was added dropwise a nicotine/ethanol solution (2 to 12 mg nicotine base). A xanthan gum solution (100 mg Keltrol®; 150 mg methyl hydroxybenzoate; and 15 mg propyl hydroxybenzoate) was then added to the complex. The pH was then adjusted to 5.5 by adding phosphate buffer (pH 7.5). The final volume was adjusted to 100 ml.

Thirty healthy volunteer adults, divided into three equal groups, will be enrolled in a study to determine the pharmacokinetics of a single dose of nicotine administered by one of the three oral routes above. In addition, all subjects will receive a single 15 microgram/kg IV dose of nicotine over 30 minutes so that the true bioavailability for each route of administration can be determined. The time interval between the two nicotine doses in each subject will be at least one week. After each dose blood samples will be obtained serially over the course of 12 hours. Plasma concentrations of nicotine will be measured. Pharmacokinetics parameters to be determined will include: Tmax; Cmax; AUC; T1/2; and bioavailability. In addition, the subject tolerability of these modes of delivery will be determined. Comparison between the 3 and 6 mg doses of Eudragit coated oral nicotine will also be made to determine if a dose response for delayed-release oral nicotine (Eudragit coated) exists.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

We claim:

1. A therapeutic method of treating inflammatory bowel disease comprising locally administering to the rectum, colon and/or terminal ileum of a patient in need of such treatment, 0.04 to 0.1 mg/kg of nicotine, or a pharmaceutically acceptable salt thereof.

2. The method of claim 1 wherein the inflammatory bowel disease is ulcerative colitis.

3. The method of claim 1 wherein the inflammatory bowel disease is Crohn's disease.

4. The method of claim 1 wherein the inflammatory bowel disease is pouchitis.

5. The method of claim 1 wherein the nicotine is administered to the lower colon of said patient by rectal enema.

6. The method of claim 5 wherein said enema comprises nicotine in combination with a hydrophobic vehicle.

7. The method of claim 1 wherein the nicotine is administered to the lower colon of said patient by rectal foam.

8. The method of claim 1, wherein the nicotine is administered by means of an orally ingested enterically coated unit dosage form comprising 0.04 to 0.1 mg/kg of nicotine which is released from the dosage form in the ileum and/or in the colon of said patient.

9. The method of claim 8 wherein the enteric coating disintegrates at about pH 7.

10. The method of claim 1 wherein the pharmaceutically acceptable salt is nicotine bitartrate.

11. A therapeutic method of treating ulcerative colitis comprising rectally administering to a patient, an enema comprising 0.04 to 0.1 mg/kg of nicotine or a pharmaceutically acceptable salt thereof.

12. A delayed release orally ingestible enteric coated dosage form comprising 3 mg to 6 mg of nicotine or pharmaceutically acceptable salt thereof which is released from the dosage form in the ileum and/or colon of a patient.

13. A therapeutic method of treating ulcerative colitis comprising orally administering to a patient an oral dosage form as claimed in claim 12.

14. An oral dosage form as claimed in claim 12, wherein the pharmaceutically acceptable salt is nicotine tartrate.

15. An oral dosage form as claimed in claim 12, wherein the enteric coating is selected from the group consisting of cellulose acetate phthalate, polyvinyl acetate phthalate, hydroxypropylmethylcellulose phthalate and methacrylic acid ester copolymers with acidic ionizable groups.

* * * * *